United States Patent [19]

Brawn et al.

[11] Patent Number: 5,185,325

[45] Date of Patent: * Feb. 9, 1993

[54] COSMETIC COMPOSITION

[75] Inventors: Peter R. Brawn, Bedford; Walter T. Gibson, Wellingborough, both of England

[73] Assignee: Chesebrough-Pond's USA Co., Division of Conopco, Inc., Greenwich, Conn.

[*] Notice: The portion of the term of this patent subsequent to May 14, 2008 has been disclaimed.

[21] Appl. No.: 798,273

[22] Filed: Nov. 20, 1991

Related U.S. Application Data

[63] Continuation of Ser. No. 368,745, Jun. 20, 1989, abandoned.

[30] Foreign Application Priority Data

Jun. 23, 1988 [GB] United Kingdom ............... 8814982
Dec. 22, 1988 [GB] United Kingdom ............... 8830018

[51] Int. Cl.$^5$ .......................... A61K 7/06; A61K 7/48
[52] U.S. Cl. ............................... 514/23; 514/62; 514/880; 514/881; 424/70
[58] Field of Search ............... 514/23, 62, 880, 881; 424/70

[56] References Cited

U.S. PATENT DOCUMENTS

| | | | |
|---|---|---|---|
| 3,887,703 | 6/1975 | Manoussos et al. | 514/880 |
| 4,139,619 | 2/1979 | Chidsey | 514/230.8 |
| 4,761,401 | 8/1988 | Couchmann et al. | 514/880 |
| 4,975,441 | 12/1990 | Gibson | 514/425 |
| 5,015,470 | 5/1991 | Gibson | 435/200 |
| 5,037,643 | 8/1991 | Green | 424/70 |
| 5,081,151 | 1/1992 | Davis et al. | 514/574 |

FOREIGN PATENT DOCUMENTS

0242967 10/1987 European Pat. Off. .
2438534 2/1976 Fed. Rep. of Germany .
2619100 11/1977 Fed. Rep. of Germany .
2824025 12/1979 Fed. Rep. of Germany .

OTHER PUBLICATIONS

Errdlender Arch. Lrogverie Pharm. 787-788 (Apr. 1939) Chem Zentr 19401, 3329-3330, Chemical Abs., vol. 36, 1942, Abstract 3910(7).
McOmie, Protective Groups in Organic Chemistry (1973, Plenum Press, New York) pp. 109-111.
Foye, Principals of Medicinal Chemistry (1981, Lea and Febiger, Philadelphia), p. 92.
Clark, The Old Farmer's Almanac, 1988, pp. 82-85.

*Primary Examiner*—Ronald W. Griffin
*Attorney, Agent, or Firm*—Milton L. Honig

[57] ABSTRACT

A composition suitable for topical application to mammalian skin or hair for inducing, maintaining or increasing hair growth comprises a glycosaminoglycanase inhibitor chosen from aldonomonolactones, alduronomonolactones and acylated monosaccharides, and a cosmetically acceptable vehicle for the inhibitor; the total amount of the inhibitor present in the composition being sufficient to increase hair growth in the rat, when said composition is applied topically thereto over a period of no more than 3 months, by at least 10% more than that obtainable using a control composition from which the said inhibitor has been omitted, in accordance with the Rat Hair Growth Test.

10 Claims, No Drawings

COSMETIC COMPOSITION

This is a continuation application of Ser. No. 07/368,745, filed Jun. 20, 1989, now abandoned.

FIELD OF THE INVENTION

The invention relates to cosmetic and pharmaceutical compositions for topical application to mammalian skin or hair, containing an enzyme inhibitor which is capable of promoting hair growth, especially terminal hair growth on the human scalp.

BACKGROUND

The Hair Growth Cycle

It should be explained that in most mammals, hair does not grow continuously, but undergoes a cycle of activity involving alternate periods of growth and rest. The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen, which is heralded by the cessation of mitosis, and during which the follicle regresses upwards through the dermis and hair growth ceases, (iii) the resting stage known as telogen, in which the regressed follicle contains a small secondary germ with an underlying ball of tightly packed dermal papilla cells.

The initiation of a new anagen phase is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth by the topical application of hair tonics and the like, with the possible exception of minoxidil, none has been shown to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is by transplantation of hair to the bald areas. This is, however, an extremely painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question comprises a pyrimidine carbamate.

It has also been reported in U.S. Pat. No. 4,139,619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth reported independently by Bazzano and Chidsey, following topical application of minoxidil or related compounds, there is general concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity. There is also evidence that certain side effects have been experienced following topical application of minoxidil.

In addition to the alleged benefits of employing the pyrimidine carbamates of Bazzano or minoxidil of Upjohn, many other hair regrowth studies have been reported in the literature. In particular, the work of Meyer et al (1961) in the Proceedings of the Society of Experimental and Biological Medicine, 108, 59-61, is worthy of mention. Meyer and his co-workers repeatedly injected acid mucopolysaccharides into the skin of shaved rabbits and reported observing the initiation of the hair growth cycle with stimulation of hair growth which in some instances appeared to be thicker than usual. They found that heparan sulphate was particularly active, while dermatan sulphate and chondroitin-6-sulphate were also active in this respect, but to a lesser extent.

It has also been reported by Frajdenrajch in EP-A-O 035 919 to include chondroitin sulphate in a hair composition in order to prevent loss and encourage growth of the hair.

Also, Shansho Seigaku in JA-59/186911 describes a shampoo containing a mucopolysaccharide such as chondroitin sulphate.

There are also other references, mainly of Japanese origin, which claim the use of chondroitin sulphate in preparations for topical application to human skin, particularly as hair tonics.

Kohler in DE OLS 24 38 534 reports that D-glucuronic acid and glucuronic acid $\gamma$-lactone (also known as glucurono-6,3-lactone) can be applied externally to the skin, together with vitamin C and water, ethanol or aqueous ethanol as a vehicle, as a scalp care agent. In a particular experiment, Kohler reports regrowth of hair following daily application for six months of a 1% solution of D-glucuronic acid.

Kohler et al in DE OLS 26 19 100 also claims the use of glucuronic acid or glucuronic acid $\gamma$-lactone as inhibitors in agents for inhibiting the activity of $\beta$-glucuronidase, particularly in combination with vitamin $B_{12}$. Whereas Kohler et al are concerned with $\beta$-glucuronidase as found in unusually high concentrations in healing wounds and cancer tissues, they do state that the agents also have a beneficial effect on the loss of hair.

BACKGROUND TO THE INVENTION

The above review of the most relevant references concerning the alleged promotion of hair growth following topical or systemic application of specified molecules, has prompted the study in greater detail, of the biological and biochemical mechanisms involved in the control of the hair growth cycle. The reported role of the dermal papilla which is situated at the base of the hair follicle, and the closely related cells of the connective tissue sheath which surrounds the hair follicle are alleged to be of key importance in governing the cyclic behaviour of hair follicles. This has been shown, for example, directly by Oliver R F (1970) J Embryol Exp Morphol., 23, 219-236, and the changes in the dermal papilla during the hair cycle are consistent with these observations. At the end of anagen, there is a sudden loss of fibronectin [Couchman J R and Gibson W T, (1985) Dev Biol., 108, 290-298] and metachromatic (glycosaminoglycan) staining [Montagna W et al, (1952) Q J Microsc Sci., 93, 241-245] from the connective tissue matrix of the dermal papilla which then undergoes condensation.

Conversely, expansion and elaboration of new matrix is associated with the onset of anagen. A direct role of matrix components in stimulating hair growth was suggested by the work of Meyer et al (1961), [supra].

It is accordingly apparent that glycosaminoglycan breakdown is an important early change in catagen, and since there is already evidence for a link between the presence of intact glycosaminoglycans and hair growth, we have suggested that prevention of glycosaminoglycan breakdown may lead to earlier onset and/or prolongation of anagen. This would effectively retard hair loss and reverse baldness.

When considering the breakdown of glycosaminoglycans, it must be remembered that these are complex polysaccharides built up from alternating hexosamine and uronic acid units. Modification of these units by N- and/or O-sulphation, and by N-acetylation provides further scope for diversity, which necessitates the concerted, sequential action of a range of enzymes for complete degradation to occur. An important mechanism involves the action of endoglycosidases, exoglycosidases and sulphatases (i.e. glycosaminoglycanases) which cleave the glycosaminoglycan molecule at specific sites. It follows that glycosaminoglycan breakdown may be prevented by inhibiting glycosaminoglycanase activity in the skin.

We have now identified molecules with such activity which are suitable and safe for topical application to human skin, and which will indeed stimulate hair growth as predicted on the basis of the theory outlined above.

DEFINITION OF THE INVENTION

Accordingly, the invention provides a composition suitable for topical application to mammalian skin or hair for inducing, maintaining or increasing hair growth which comprises:

(i) a glycosaminoglycanase inhibitor chosen from:

(a) aldonomonolactone or alduronomonolactone derivatives having the structure:

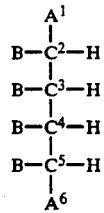

Where $A^1$ is

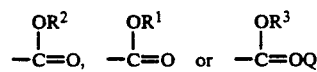

$A^6$ is

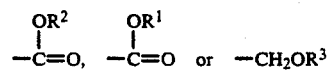

B is $-OR^3$, $-NHR^3$, $-NHR^4$, or a lactone linkage to position 1 or 6, and/or another linkage to Q;

said substituents B being the same or different, and being in either configuration, with respect to the backbone of the above structure, on positions $C^2$ to $C^5$ not involved in a lactone ring;

and where $R^1$ is $-H$, $C_1$ to $C_{20}$ alkyl, a metal cation, $NH_4^+$ or an alkanolamine cation;

$R^2$ is the remainder of the molecule joined through another C atom at positions 2 to 5 to form a lactone;

$R^3$ is $-H$, $-CH_3$, benzyl or $C_2$ to $C_6$ acyl;

$R^4$ is $-H$, $-CH_3$, benzyl or $C_3$ to $C_6$ acyl;

Q is the remainder of the molecule joined through an ether linkage to either $C^4$ or $C^5$, forming either a pyranose or a furanose ring;

provided that, when $A^1$ is

then $A^6$ is

provided also that, when $A^6$ is $CH_2OH$, then one or more of the B substituents is $-CH_3$, $C_2$ to $C_4$ acyl or $NHR^4$;

provided also that when $A^1$ is

and all B substituents are $-OH$, then $A^6$ is

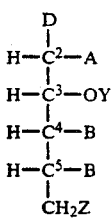

or —CH$_2$OR$^3$, and R$^1$ is C$_1$ or C$_9$ to C$_{20}$ alkyl;

(b) acylated monosaccharides having the structure:

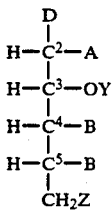

where A or —OY or —NHR$^5$
B is —OY, or an ether linkage to D,
D is

where X is an ether linkage
either to C$^4$ or C$^5$ forming a pyranose or furanose ring;
Y is —H, —SO$_3$M, C$_2$ to C$_4$ acyl or C$_1$ to C$_{18}$ alkyl;
said substituents A, B and —OY being the same or different, and being in either configuration, with respect to the backbone of the structure;
and where
Z is —H or —OY
R$^5$ is —H, —SO$_3$M or C$_3$ or C$_4$ acyl,
M is —H, a metal cation, NH$_4$+ or an alkanolamine cation;
provided that, when R$^5$ is —H, then 1 or more of Y is chosen from —SO$_3$M or C$_2$ to C$_4$ acyl; and mixtures thereof; and (ii) a cosmetically acceptable vehicle for the inhibitor; the total amount of the inhibitor present in the composition being sufficient to increase hair growth in the rat, when said composition is applied topically thereto over a period of no more than 3 months, by at least 10% more than that obtainable using a control composition from which the said inhibitor has been omitted, in accordance with the Rat Hair Growth Test.

The term "glycosaminoglycanse inhibitor" is intended to include precursors thereof, which are molecules suitably modified, for example by esterification, to protect them and to enhance their delivery through the skin to the hair follicle. It is believed that enzymes, such as esterases, which occur naturally in the skin, remove the protecting groups to yield the active inhibitor. It is also believed that other physiological mechanisms may similarly be involved.

DISCLOSURE OF THE INVENTION

The Glycosaminoglycanase Inhibitor

According to the invention, the composition comprises a glycosaminoglycanase inhibitor chosen from derivatives of aldonomonolactones and alduronomonolactones, and also acylated monosaccharides, and mixtures thereof.

These enzyme inhibitors, together with specific examples thereof, can be expressed as follows:

(a) aldonomonolactone or alduronomonolactone derivatives having the structure:

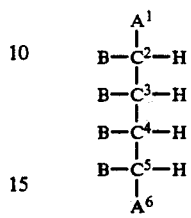

where
A$^1$ is

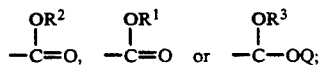

A$^6$ is

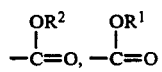

B is OR$^3$, NHR$^3$, NHR$^4$ or a lactone linkage to position 1 to 6, and/or an ether linkage to Q;
said substituents B being the same or different, and being in either configuration, with respect to the backbone of the above structure, on positions C$^2$ to C$^5$ not involved in a lactone ring;
and where R$^1$ is —H, C$_1$ to C$_{20}$ alkyl, a metal cation, NH$_4$+ or an alkanolamine cation;
R$^2$ is the remainder of the molecule joined through another C atom at positions 2 to 5 to form a lactone;
R$^3$ is —H, —CH$_3$, benzyl or C$_2$ to C$_6$ acyl;
R$^4$ is —H, —CH$_3$, benzyl or C$_3$ to C$_6$ acyl;
Q is the remainder of the molecule joined through an ether linkage to either C$^4$ or C$^5$, forming either a pyranose or furanose ring;
provided that, when A$^1$ is

then A$^6$ is

provided also that, when A$^6$ is CH$_2$OH, then one or more of the B substituents is —CH$_3$, C$_2$ to C$_4$ acyl or NHR$^4$;
provided also that, when A$^1$ is

and all B substituents are —OH, then
A$^6$ is $$\begin{array}{c} OR^1 \\ | \\ -C=O \end{array}$$

or $CH_2OR^3$, and $R^1$ is $C_1$ or $C_9$ to $C_{20}$ alkyl; Preferred examples of aldonomonolactone derivatives which inhibit glycosaminoglycanases are as follows, where:

|  | Inhibitor No in Examples |
|---|---|
| 6-acetyl-galactono-1,4-lactone | 1 |
| 6-propionyl-galactono-1,4-lactone | 2 |
| 6-butyryl-galactono-1,4-lactone | 3 |
| 2-propionamido-2-deoxygluconolactone | 4 |
| 2-butyramido-2-deoxygluconolactone | 5 |
| 2-propionamido-2-deoxygalactonolactone | 6 |
| 2-butyramido-2-deoxygalactonolactone | 7 |
| 6-propionyl-2-acetamido-2-deoxygluconolactone | 8 |
| diacetyl-6-propionyl-2-acetamido-2-deoxygluconolactone | 9 |
| 6-butyryl-2-acetamido-2-deoxygalactonolactone | 10 |
| diacetyl-6-butyryl-2-acetamido-2-deoxygalactonolactone | 11 |
| 2,3,5,6-tetraacetyl-galactono-1,4-lactone | 12 |
| 2,3,5-triacetyl-6-propionylgalactono-1,4-lactone | 13 |
| triacetyl-2-propionamido-2-deoxygalactonolactone | 14 |
| triacetyl-2-butyramido-2-deoxygluconolactone | 15 |
| 6-methyl-glucaro-1,4-lactone | 16 |
| 2,3,5,6-tetramethyl-glucaro-1,4-lactone | 17 |
| 6-methyl-2,3,5-triacetylglucaro-1,4-lactone | 18 |
| 6-methyl-3-methyl-glucaro-1,4-lactone | 19 |
| 6-methyl-3-acetyl-glucaro-1,4-lactone | 20 |

A preferred example of an alduronomonolactone derivative which inhibits glycosaminoglycanases is:

| 1,2,5-triacetyl-glucurono-6,3-lactone | 21 |
|---|---|

(b) acylated monosaccharides having the structure:

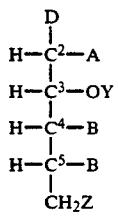

where A is —OY or —NHR$^5$
B is —OY, or an ether linkage to D,
D is

where X is an ether linkage
either to $C^4$ or $C^5$ forming a pyranose or furanose ring;
Y is —H, —SO$_3$M, $C_2$ to $C_4$ acyl or $C_1$ to $C_{18}$ alkyl; said substituents A, B and —OY being the same or different, and being in either configuration, with respect to backbone of the above structure;
and where
Z is —H or —OY
R$^5$ is —H, —SO$_3$M or $C_3$ or $C_4$ acyl,
M is —H, a metal cation, NH$_4$+, or an alkanolamine cation;

provided that, when R$^5$ is —H, then 1 or more of Y is chosen from —SO$_3$M or $C_2$ to $C_4$ acyl; and mixtures thereof.

Preferred examples of acylated monosaccharides which inhibit glycosaminoglycanases are as follows:

|  | Inhibitor No in Examples |
|---|---|
| 2-propionamido-2-deoxyglucose | 22 |
| 1,3,4,6-tetraacetyl-2-propionamido-2-deoxyglucose | 23 |
| 2-butyramido-2-deoxygalactose | 24 |
| 1,3,4,6-tetraacetyl-2-butyramido-2-deoxygalactose | 25 |
| 2-sulphamido-2-deoxygalactose | 26 |
| 2-sulphamido-2-deoxyglucose | 27 |
| 2-butyramido-2-deoxymannose | 28 |
| 1,3,4,6-tetraacetyl-2-butyramido-2-deoxymannose | 29 |
| 2-butyramido-2-deoxyglucose | 30 |
| 1,3,4,6-tetraacetyl-2-butyramido-2-deoxyglucose | 31 |

The total amount of glycosaminoglycanase inhibitor present in the composition according to the invention is sufficient to increase hair growth in the rat, the model selected for this test, when said composition is applied topically thereto over a period of no more than 3 months, by at least 10% more than that obtainable using a control composition from which the said inhibitor has been omitted, in accordance with the Rat Hair Growth Test.

Preferably, the amount of inhibitor should be sufficient to increase hair growth in the rat by at least 20%, more preferably by at least 30%, most preferably by at least 40% and ideally by at least 50%.

The sufficient amount will depend on the effectiveness of the inhibitor some being more effective than others, but in general, an amount of from 0.0001 to 99%, preferably from 0.1 to 20% by weight of the composition will provide an adequate dose to the skin after topical application.

The Vehicle

The composition according to the invention also comprises a solid, semi-solid or liquid cosmetically and/or physiologically acceptable vehicle, to enable the inhibitor to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the chemical inhibitors which therefore ensure that they can be applied to and distributed evenly over the hair and/or scalp at an appropriate concentration. The vehicle is preferably one which can aid penetration of the inhibitors into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, metnylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of a selected inhibitor to the skin in an amount which is sufficient effectively to enhance hair growth. The amount of the vehicle can comprise the balance of the composition, particularly where little or no other ingredients are present in the composition. Accordingly, the vehicle or vehicles can comprise from 1 to 99.99%, preferably from 50 to 99.5% and ideally from 90 to 99% by weight of the composition.

Perfume

The composition according to the invention can also optionally comprise a perfume in an amount sufficient to make the composition acceptable to the consumer and pleasant to use. Usually, the perfume will form from 0.01 to 10% by weight of the composition.

Activity Enhancer

The composition according to the invention can also optionally comprise an activity enhancer.

The activity enhancer can be chosen from a wide variety of molecules which can function in different ways to enhance the hair growth effects of the glycosaminoglycanase inhibitor. Particular classes of activity enhancers include other hair growth stimulants, penetration enhancers and cationic polymers, whose presence can further improve the delivery of the inhibitor through the stratum corneum to its site of action in the immediate environment of the hair follicle.

Some activity enhancers can also function as vehicles for the inhibitor.

(a) Other Hair Growth Stimulants i) Examples of other substances which themselves possess the ability to stimulate or increase hair growth include, for example;
Benzalkonium chloride
Benzethonium chloride
Phenol
Estradiol
Diphenhydramine hydrochloride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Panthenol
Castor oil
Hinokitiol
Prednisolone
Resorcinol ii) Further substances which themselves possess the ability to increase the rate of terminal hair growth include:

$\alpha$-1,4 esterified disaccharides described by Choay S.A. in EP-A-O 064 012, having the structure:

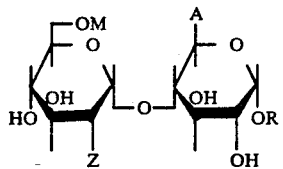

where

Z represents a functional nitrogen group, such as an azide or a group having the structure —NHB, in which B represents —H or a functional group such as acetyl or sulphate as a salt with an organic or mineral cation;

M represents —H or $SO_3M_1$, where $M_1$ is an organic or metallic cation, particularly an alkali metal; or an acetyl group;

R represents a $C_1$ to $C_4$ alkyl radical, especially methyl; or an aryl radical;

A represents a functional group such as an acid or —$COOR_1$, where $R_1$ represents —H or a $C_1$ to $C_4$ alkyl radical, especially methyl; or a metal, especially an alkali metal;

esterified oligosaccharides as described by Unilever in EP-A-O 211 610, including at least one esterified disaccharide unit consisting of a uronic acid residue having the structure:

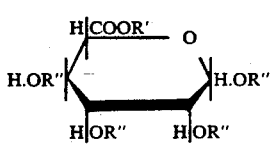

and a hexosamine residue having the structure:

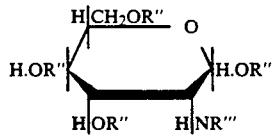

where
R' is —H, $C_3$ to $C_{10}$ alkyl or

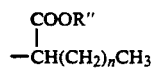

R" is —H, $C_1$ to $C_4$ alkyl, —CO(CH$_2$)$_m$CH$_3$, —SO$_3$M,
R''' is —H, —CO(CH$_2$)$_m$CH$_3$, or —SO$_3$M,
M is —H, or a metallic or organic cation
n is 0 or an integer of from 1 to 7, and
m is 0 or the integer 1 or 2;
the groups designated R" being the same or different, one R" group from each pyranose ring structure being linked by a glycosidic linkage having the configuration α-1,3, β-1,4, β-1,3 or β-1,4; and the —COOR', —CH$_2$OR"
and —OR" groups being of either configuration with respect to the pyranose rings;

iii) Minoxidil glucuronides, as described by Unilever in EP-O 242 967, iv) Minoxidil sulphates, as described by The Upjohn Co. in WO 86/04231, and v) Minoxidil, and other derivatives thereof as described by The Upjohn Co, in U.S. Pat. No. 4 139 619.

Particularly preferred mixtures of minoxidil and a glycosaminoglycanase inhibitor according to the invention include the following:

Minoxidil and 6-propionyl-2-acetamido-2-deoxygluconolactone

Minoxidil and diacetyl-6-propionyl-2-acetamido-2-deoxygluconolactone

Minoxidil and 6-butyryl-2-acetamido-2-deoxygalactonolactone (vi) Direct proteoglycanase inhibitors, such as 1,10-phenanthroline.

(vii) Glycosaminoglycanase inhibitors, such as aldonolactones and esterified aldonolactones having the structure:

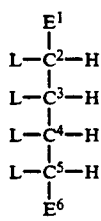

where
$E^1$ and $E^6$ are —H,

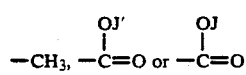

L is —OJ" or a lactone linkage to position 1 or 6, or —NHCOCH$_3$ and where
J is —H or $C_2$ to $C_8$ alkyl,
J' is the remainder of the molecule joined through another C atom at positions 2 to 5 to form a lactone,
J" is —H or $C_2$ (i.e. acetyl) to $C_4$ acyl of either configuration with respect to the backbone of this molecule;
preferred examples of which include:
L-Galactono-1,4-lactone
L-Arabino-1,5-lactone
D-Fucono-1,5-lactone
D-Glucaro-1,4-lactone
D-Glucurono-6,3-lactone
Galactaric acid lactone
2-Acetamido-2-deoxygluconolactone
2-Acetamido-2-deoxygalactono-lactone
D-Glucaro-1,4:6,3-dilactone
L-Idaro-1,4-lactone
2,3,5-Tri-0-acetyl-D-glucaro-1,4-lactone
2,5-Di-0-acetyl-D-glucaro-1,4:6,3-dilactone (viii) Glycosaminoglycanase inhibitors, such as monosaccharides and esterified monosaccharides having the structure:

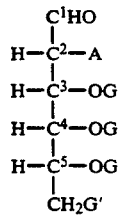

where
A is —OG or —NHCOCH$_3$
G is —H, —SO$_3$M", $C_2$ (i.e. acetyl) to $C_4$ acyl
G' is —H or —OG
M" is —H or a metal cation
wherein the functional groups can be in either configuration with respect to the backbone of the above molecule;
preferred examples of which include:
N-Acetylglucosamine
N-Acetylgalactosamine
D-Galactosamine
D-Glucosamine-3-sulphate
N-Acetylmannosamine (ix) glycosaminoglycan chain cellular uptake inhibitors such as, hexuronic acid and esters thereof which may be represented by the generic structure:

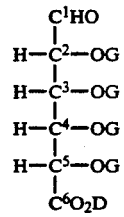

where
G is —H, —SO$_3$M", $C_2$ (i.e. acetyl) to $C_4$ acyl;
D is —H or $C_2$ to $C_8$ alkyl
M" is —H or a metal cation;
wherein the functional groups can be in either configuration with respect to the backbone of the above molecule;

(x) Chemical inhibitors of glycosidase activity chosen from lactams having the structure:

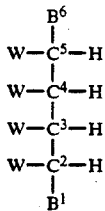

where
B¹ and B⁶ are —H, —CH₃,

—CH₂OT or

B¹ and B⁶ being the same or different, and at least one of which being the group:

in a lactam ring;
and where
W is —OT', —NHT' or a lactam linkage to B¹ or B⁶;
the W groups being the same or different, and at least one of which is involved in a lactam linkage;
and where
T is the same or different and is chosen from —H, —C$_p$H$_{2p+1}$ or a metal ion,
T' is —H or —COC$_p$H$_{2p+1}$, and
p is an integer of from 1 to 22;
provided that:
where any of the W groups is —OT' or —NHT', then that group or groups can be of either stereochemical configuration with respect to the plane of the ring,
preferred examples of which include:
D-glucaro-1,5-lactam
L-Galactono-1,4-lactam,
L-Arabino-1,5-lactam,
D-Fucono-1,5-lactam, D-Glucaro-1,4-lactam,
D-Glucurono-6,3-lactam,
1,2,5-tri-0-acetyl-D-glucurono-6,3-lactam
2-Acetamido-2-deoxygluconolactam,
2-Acetamido-2-deoxygalactonolactam,
D-Glucaro-1,4:6,3-dilactam,
L-Idaro-1,4-lactam,
2,3,5-Tri-0-acetyl-D-glucaro-1,4-lactam,
2,5-Di-0-acetyl-D-Glucaro-1,4:6,3-dilactam,
D-glucaro-1,5-lactam ethyl ester;
(xi) chemical activators of protein kinase C enzymes chosen from diacylglycerols having the structure:

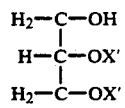

where X' is the same or different and is represented by the grouping:

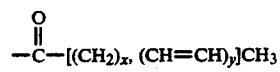

where x is 0 or an integer of from 1 to 28, and
y is 0 or an integer of from 1 to 5;
the R groups being of either stereochemical configuration with respect to the carbon backbone of the glycerol molecule, the double bonds being of either cis or trans configuration;
preferred examples of which include:
1,2-Dibutanoyl-rac-glycerol
1,2-Dihexanoyl-sn-glycerol
1,2-Dioctanoyl-rac-glycerol
1,2-Dioctanoyl-sn-glycerol
1,2-Didecanoyl-rac-glycerol
1-Oleoyl-2-acetyl-rac-glycerol
1-Oleoyl-2-acetyl-sn-glycerol
1-Stearoyl-2-arachidonoyl-sn-glycerol
1,2-Distearoyl-rac-glycerol
1,2-Dipentadecanoyl-sn-glycerol
1,2-dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac-glycerol, and
1,2-Dioctaeicosanoyl-sn-glycerol.

(b) Penetration Enhancers

As has been stated earlier, the presence of a penetration enhancer can potentiate the benefit of the inhibitor, by improving its delivery through the stratum corneum to its site of action in the immediate environment of the hair follicle close to the dermal papilla.

The penetration enhancer can accordingly function in a variety of ways. It can for example, improve the distribution of the hair growth promoter on the skin surface or, it can increase its partition into the skin from the composition when applied topically, so aiding its passage to its site of action. Other mechanisms enhancing the benefit of the inhibitor may also be involved.
Examples of penetration enhancers include:
2-methyl propan-2-ol
Propan-2-ol
Ethyl-2-hydroxypropanoate
Hexan-2,5-diolPOE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
2-hydroxypropanoic acid
2-hyroxyoctanoic acid, Yet further penetration enhancers include esters of pyroglutamic acid having the structure:

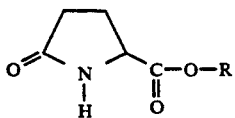

where
R is $C_1$ to $C_{30}$ alkyl, or

and where T' and T" are the same or different and are each represented by H or the grouping:

$$[(CH_3)_u, (CH_2OH)_v, (CH_2)_w, (CH_3CH_2)_x, (CH=CH)_z]—$$ (2)

where
u is zero or 1
v is zero, or the integer 1 or 2,
w is zero, or an integer of from 1 to 21
x is zero, or an integer of from 1 to 4,
y is zero, or the integer 1 or 2,
z is zero, or an integer of from 1 to 22, and
u+v+w+x+y+z is an integer of from 1 to 22;
provided that when the subgrouping (CH=CH) is present, then the total number of carbon atoms in said grouping is from 10 to 22.

Examples of suitable esters of pyroglutamic acid where R in structure (1) is $C_1$ to $C_{30}$ alkyl are:
pyroglutamic acid methyl ester
pyroglutamic acid ethyl ester
pyroglutamic acid n-propyl ester
pyroglutamic acid n-butyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradcyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester Particularly preferred esters of this group are those where R in structure (1) is $C_1$ to $C_{14}$ alkyl, (linear or branched), especially $C_1$ to $C_6$ (linear or branched).

Further examples of preferred esters of pyroglutamic

are those where T' and/or T" having the structure shown for grouping (2), include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl, and
arachidyl.
and the $C_{10-22}$ alkenyl groups:
linoleyl
linolenyl
α-linolenyl arachidonyl, and
columbinyl.

Further examples of the grouping (2) also include hydroxyalkyl groups having from 1 to 22 carbon atoms, such as:

hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

It is to be understood that the above list is not exhaustive, there being many other examples of alkyl or substituted alkyl groups expressed by the above generic grouping (2).

Further specific examples of esters of pyroglutamic acid which are particularly suited to use as penetration enhancers are:

2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above lists of specific examples of esters of pyroglutamic acid are not exhaustive, there being many other examples expressed by the generic structure of these esters.

Further examples of penetration enhancers include:
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one Further examples of penetration enhancers include liposomes which can be employed to encapsulate the glycosaminoglycanase inhibitors as herein defined. Accordingly, liposomes formed from any lipid material conventionally employed in the art and of a wide variety of sizes can be incorporated in the composition according to the invention, in order to enhance the delivery of the inhibitors to the skin.

Further examples of penetration enhancers include surface active agents, preferred examples of which include:

(i) Anionic surface active agents, such as metallic or alkanolamine salts of fatty acids for example sodium laurate and triethanolamine oleate;

alkyl benzene sulphonates, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinates, for example sodium dioctyl sulphosuccinate;
monoglyceride sulphates, for example sodium glyceryl monostearate monosulphate;
isethionates, for example sodium isethionate;
methyl taurides, for example Igepon T;
acylsarcosinates, for example sodium myristyl sarcosinate;
acyl peptides, for example Maypons and Lamepons;
acyl lactylates,
polyalkoxylated ether glycollates, for example trideceth-7 carboxylic acid;
phosphates, for example sodium dilauryl phosphate.

(ii) Cationic surface active agents, such as amine salts, for example sapamin hydrochloride;
quartenary ammonium salts, for example Quaternium 5, Quaternium 31 and Quaternium 18;

(iii) Amphoteric surface active agents, such as imidazol compounds, for example Miranol;
N-alkyl amino acids, such as sodium cocaminopropionate and asparagine derivatives;
betaines, for example cocoamidopropylbetaine (iv) Nonionic surface active agents, such as fatty acid alkanolamides, for example oleic ethanolamide;
esters of polyalcohols, for example Span;
polyglycerol esters, for example that esterified with $C_{12-18}$ fatty acids and one or several OH groups;
polyalkoxylated derivatives, for example polyoxy:- polyoxyethylene stearate, and octylphenoxy polyethoxyethanol (TRITON X-100);
ethers, for example polyoxyethylene lauryl ether;
ester ethers, for example Tween;
amine oxides, for example coconut and dodecyl dimethyl amine oxides.

Mixtures of two or more of the above surface active agents can be employed in the composition according to the invention.

(c) cationic polymers chosen from:
Guar Hydroxypropyltrimonium chloride
Quaternium-19
Quaternium-23
Quaternium-40
Quaternium-57
Poly(dipropyldiallylammonium chloride)
Poly(methyl-$\beta$-propaniodiallylammonium chloride)
Poly(diallylpiperidinium chloride)

Poly(vinyl pyridinium chloride)
Quaternised poly (vinyl alcohol)
Quaternised poly (dimethylaminoethylmethacrylate); and
mixtures thereof The amount of activity enhancer, when employed in accordance with the invention, will normally be from 0.1 to 50%, preferably from 0.5 to 25% and most preferably from 0.5 to 10% by weight of the composition.

Other Hair Growth Promoter Adjuncts

The composition according to the invention can also contain adjuncts other than those already mentioned, depending on the form of the intended product. It is, for example, possible to include antiseptics, preservatives, antioxidants, emulsifiers and colouring agents, which can improve the stability and consumer appeal of the composition.

The composition according to the invention can also be employed as a vehicle for a wide variety of cosmetically or pharmaceutically active ingredients, particularly ingredients which have some beneficial effect other than the promotion of hair growth when applied to the skin.

Preservation of the Composition

The composition according to the invention is preferably preserved in such a manner that it will enjoy an extended shelf life following manufacture and prior to sale and use. Ideally the composition will have an indefinite shelf life.

It is accordingly apparent that the glycosaminoglycanase inhibitor is likely to be prone to attack by bacteria, moulds and fungi and other microbial influences, particularly at pH values near neutrality that characterise the preferred composition. The shelf-life of the composition can therefore be unacceptably short due to the biodegradation of the inhibitor unless steps are taken to preserve the composition.

In order to be preserved, the composition should preferably be free, or substantially free, from viable microbial contaminants that are capable of resulting in microbial spoilage of the composition, and/or biodegradation of the inhibitor prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of methods that can be employed to achieve preservation of the composition, includes the following:

(i) Sterilisation

The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.

(ii) Chemical Preservative

The composition according to the invention can also be preserved by including in it a chemical preservative which functions to prevent the growth of or kill bacteria, fungi or other microorganisms. Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.

(iii) Water Activity Depressants

The composition according to the invention can also be preserved by the inclusion of a water activity depressant such as glycerol, propylene glycol, sorbitol, sugars and salts, for examples alkali metal halides, sulphates and carboxylates. When employing a water activity depressant, sufficient should be incorporated in the composition according to the invention to reduce the water activity ($a_w$) from 1 to <0.9, preferably to <0.85 and most preferably <0.8, the lowest of these values being that at which yeasts, moulds and fungi will not proliferate.

Process

The invention also provides a process for the preparation of a composition suitable for topical application to mammalian skin or hair which comprises mixing an inhibitor as herein defined, with a suitable vehicle to provide a composition according to the invention, in which the inhibitor forms from 0.0001 to 99% by weight of the composition.

Product Form and Container

The compositions of the invention can be formulated as liquids, for example as a lotion, shampoo, milk or cream for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

Use of the Glycosaminoglycanase Inhibitor for Inducing, Maintaining or Increasing Hair Growth The invention also provides for the use of an inhibitor, as herein defined, for topical application to mammalian skin or hair for inducing, maintaining or increasing hair growth.

The compositions according to the invention are primarily intended for topical application to the scalp of the human subject, particularly where the head is already bald or balding, in order to promote the regrowth of terminal hair. The compositions can also be applied profilactically to the hair and hence the scalp to reduce or prevent the onset of baldness.

The amount of the composition and the frequency of application to the hair and/or scalp can vary widely, depending on personal needs, but it is suggested as an example that topical application of from 0.1 to 5 g daily containing from 0.00001 to 1 g of a selected chemical inhibitor over the period of at least six months will in most cases result in an improvement in hair growth.

EVALUATION OF EFFICACY OF GLYCOSAMINOGLYCANASE INHIBITORS USING THE RAT MODEL

The Rat Hair Growth Test

The effect of compounds on hair growth was assessed using male albino Wistar rats as an animal model. The rats were chosen from as few litters as possible and were each approximately 42 days of age at the start of the test. Each rat was housed individually to prevent licking.

In each comparison, 10 rats were used in each group and hair growth was assessed as follows:

A small patch of normal skin (4 cm×4 cm) on the upper back of each rat was clipped at the start and 0.3 ml of a hair growth stimulant composition (or a control) applied topically twice daily and once on Saturdays and Sundays to each clipped area. The concentration of test compound in the composition was chosen from 0.1 to 20% by weight.

It is to be understood that the potency of each of the inhibitors in terms of its ability to induce, maintain or increase hair growth is unlikely to be uniform, some being more potent than others, and therefore the concentration of any inhibitor chosen for thorough evaluation must be carefully selected after preliminary testing to determine its potential as a hair growth promotor. In any case, this concentration will lie within the range of from 0.1 to 20% by weight as stipulated above.

Hair was clipped from the area of the patch twice weekly, collected and weighed at each time point over a standard period of 3 months, and cumulative hair weight calculated. From these data, it was possible to estimate the effect of a hair growth stimulant as a test compound on the amount and duration of hair growth during the experiment. A positive response, i.e. an increase of at least 10% by weight of hair after 3 months treatment, compared with a control indicates the potential of the test compound to prevent hair loss and/or reverse baldness in human subjects.

Accordingly, when the glycosaminoglycanase inhibitors, as herein defined, are assessed either individually or in combination as test compound by the Rat Hair Growth Test, an increase of at least 10% by weight of hair after 3 months treatment will be obtained. Usually, the 10% by weight minimum value will be attained well before the end of this 3 months period.

EXAMPLES

The invention is illustrated by the following examples:

EXAMPLE 1

This Example illustrates a lotion according to the invention which is suitable for topical application to the scalp in order to promote hair growth.

The lotion has the following formulation:

|  | % w/w |
| --- | --- |
| Inhibitor No. 1 | 0.1 |
| ethanol | 99.995 |
| perfume | q.s. |

EXAMPLE 2

This Example illustrates a hair tonic which is suitable for application to hair or scalp.

The hair tonic has the following formulation:

|  | % w/w |
| --- | --- |
| Inhibitor No. 2 | 0.8 |
| ethanol | 50 |
| water | 49 |
| perfume | q.s. |

EXAMPLE 3

This Example also illustrates a lotion which is suitable for topical application to the scalp.

The lotion has the following formulation:

|  | % w/w |
| --- | --- |
| Inhibitor No. 3 | 1.5 |
| propan-2-ol | 10 |
| ethanol | 88.5 |
| perfume | q.s. |

EXAMPLE 4

This Example also illustrates a hair tonic which is suitable for application to hair or scalp.

The hair tonic has the following formulation:

|  | % w/w |
| --- | --- |
| Inhibitor No. 4 | 0.2 |
| ethanol | 40 |
| water | 59.80 |
| perfume | q.s. |

EXAMPLES 5 TO 8

The following formulations represent lotions which can be used topically in the treatment of bald or balding male or female heads.

|  | % w/w | | | |
| --- | --- | --- | --- | --- |
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Inhibitor No. 5 | 5 | — | — | — |
| Inhibitor No. 6 | — | 1 | — | — |
| Inhibitor No. 7 | — | — | 0.8 | — |
| Inhibitor No. 8 | — | — | — | 0.6 |
| Perfume | 1 | 1 | 1 | 1 |
| Water to | 100 | 100 | 100 | 100 |

EXAMPLES 9 TO 12

The following formulations represent creams which can be used in the treatment of baldness.

|  | % w/w | | | |
| --- | --- | --- | --- | --- |
|  | 9 | 10 | 11 | 12 |
| Cetyl alcohol polyoxyethylene (10) | 4 | 4 | 4 | 4 |
| Cetyl alcohol | 4 | 4 | 4 | 4 |

-continued

|  | % w/w | | | |
|---|---|---|---|---|
|  | 9 | 10 | 11 | 12 |
| Mineral oil | 4 | 2 | — | — |
| Paraffin wax | — | 2 | 4 | — |
| Partial glyceride of palmitic and stearic acids | — | — | — | 4 |
| Inhibitor No. 9 | 2 | — | — | — |
| Inhibitor No. 10 | — | 1.5 | — | — |
| Inhibitor No. 11 | — | — | 2 | — |
| Inhibitor No. 12 | — | — | — | 1 |
| Minoxidil | 0.5 | 0.5 | 0.5 | 0.5 |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water to | 100 | 100 | 100 | 100 |

EXAMPLE 13

This Example illustrates a water-in-oil high internal phase emulsion containing a glycosaminoglycanase inhibitor according to the invention.

The emulsion consisted of 10% by volume oily phase and 90% by weight aqueous phase.

The oily phase and the aqueous phase had the following constitution:

|  | % w/w |
|---|---|
| Oily phase | |
| Sorbitan monooleate | 20 |
| Quaternium-18 hectorite | 5 |
| Liquid paraffin | 75 |
| Aqueous phase | |
| Inhibitor No. 13 | 0.5 |
| Xanthan gum | 1 |
| Preservative | 0.3 |
| Perfume | q.s. |
| Sodium chloride (1% w/w solution) to | 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 14 to 20 illustrate shampoos for use in washing the hair and scalp, and for promoting hair growth on the scalp.

EXAMPLE 14

|  | % w/w |
|---|---|
| Sodium lauryl ether sulphate (2 EO) [21% AD] | 41.4 |
| Lauryl dimethylamino acetic acid betaine: [30% AD] | 4 |
| Coconut fatty acid diethanolamine | 1.5 |
| Oleyl triethoxy phosphate (BRIPHOS 03D) | 1 |
| Polyglycol-polyamine condensation resin (POLYQUART H) [50% active] | 1.5 |
| Preservative, colouring matter, salt | 0.58 |
| Inhibitor No. 14 | 5 |
| Perfume | q.s. |
| Water to | 100 |

EXAMPLE 15

|  | % w/w |
|---|---|
| Sodium lauryl ether sulphate (2 EO) [100% AD] | 12 |
| POLYMER JR400 | 2.5 |
| BRIPHOS 03D | 2.5 |
| Inhibitor No. 15 | 4 |
| Magnesium Sulphate | 5 |
| Perfume | q.s. |
| Water to | 100 |

EXAMPLE 16

This Example also illustrates a lotion which is suitable for topical application to the scalp.

The lotion has the following formulation:

|  | % w/w |
|---|---|
| Inhibitor No. 16 | 1.5 |
| propan-2-ol | 10 |
| ethanol | 88.5 |
| perfume | q.s. |

EXAMPLE 17

This Example also illustrates a hair tonic which is suitable for application to hair or scalp.

The hair tonic has the following formulation:

|  | % w/w |
|---|---|
| Inhibitor No. 17 | 0.2 |
| ethanol | 40 |
| water | 59.80 |
| perfume | q.s. |

EXAMPLE 18

|  | % w/w |
|---|---|
| Monoethanolamine lauryl sulphate: [100% AD] | 20 |
| JAGUAR C13S | 3 |
| BRIPHOS 03D | 1.7 |
| Coconut diethanolamide | 5 |
| Inhibitor No. 18 | 1 |
| Zinc gluconate | 3 |
| Perfume | q.s. |
| Water to | 100 |
| pH adjusted to 6.5 | |

EXAMPLE 19

|  | % w/w |
|---|---|
| Sodium lauryl ether sulphate (3 EO): [100% AD] | 12 |
| JAGUAR C13S | 0.3 |
| BRIPHOS 03D | 1 |
| Inhibitor No. 19 | 2 |
| Sodium chloride | 4 |
| Perfume | q.s. |
| Water to | 100 |
| pH adjusted to 6.5 | |

EXAMPLE 20

|  | % w/w |
|---|---|
| Sodium lauryl ether sulphate (2 EO) [100% AD] | 12 |
| POLYMER JR400 | 3 |
| BRIPHOS O3D | 1 |
| Opacifier | 9 |
| Inhibitor No. 20 | 5 |
| Perfume | q.s |
| Water to | 100 |
| pH adjusted to 6.5 | |

EXAMPLES 21

This example illustrates a powder composition according to the invention which can be applied topically to the scalp.

|  | % w/w |
|---|---|
| Chemically modified starch | 5 |
| Chemically modified cellulose | — |
| Boric acid | 10 |
| Zinc oxide | 5 |
| Inhibitor No. 21 | 3 |
| Minoxidil glucuronide | 5 |
| Perfume | q.s. |
| Chalk | 10 |
| Talc to | 100 |

EXAMPLE 22

The following example illustrates a lotion according to the invention which can be applied topically to the scalp to prevent hair loss and stimulate hair regrowth.

|  | % w/w |
|---|---|
| Inhibitor No. 22 | 7 |
| Minoxidil | 0.2 |
| ethanol | 16 |
| citric acid | 1.05 |
| water to | 100 |
| pH adjusted to 4.2 with sodium hydroxide | |

EXAMPLES 23 & 24

These examples illustrate hair tonics which are suitable for application to the hair and scalp.

The hair tonics had the following formulation:

|  | % w/w | |
|---|---|---|
|  | 23 | 24 |
| Inhibitor No. 23 | 2 | — |
| Inhibitor No. 24 | — | 3 |
| Minoxidil | 1 | 1 |
| ethanol | 50 | 50 |
| water | 48 | 47 |
| perfume | q.s. | q.s. |

EXAMPLE 25

This example illustrates a microgel which is suitable for topical application to hair or scalp.

The gel had the following formulation:

|  | % w/w |
|---|---|
| A. Polyoxyethylene (10) oleyl ether | 14.5 |
| Polyoxyethylene fatty glyceride | 14.5 |
| Light liquid petroleum | 13.7 |
| Propylene glycol | 7.6 |
| Sorbitol | 5.9 |
| Inhibitor No. 25 | 4 |
| B. Perfume | q.s. |
| C. Water to | 100 |

This microgel was prepared by heating part A to 90° C. and part C to 95° C. and then adding part C to part A with stirring. Part B was then added at 70° C. and the final mixture cooled and poured into jars at 55° C. to 60° C. On further cooling, a gel was formed.

EXAMPLE 26

This example illustrates a shampoo which is suitable for topical application to hair in order to cleanse it, at the same time delivering an inhibitor to the scalp to enhance hair growth or regrowth.

The shampoo had the following formulation:

|  | % w/w |
|---|---|
| Triethanolamine lauryl sulphate | 16.8 |
| Coconut diethanolamide | 3.0 |
| Hydroxypropylmethyl-cellulose (1) | 0.25 |
| Corn syrup (80% solids) (2) | 20.5 |
| Dimethylpolysiloxane (3) | 1.0 |
| Cationic cellulose (4) | 0.5 |
| Ethyl alcohol (SDA 40) | 9.0 |
| Vinyl carboxy polymer (5) | 0.75 |
| Inhibitor No. 26 | 1 |
| Perfume, colour, preservative | q.s. |
| Water to | 100 |
| Acid or base to pH: | 6.5 |

(1) Methocel E4M (Dow Chemical)
(2) 42 Dextrose equivalent (Staley 1300)
(3) 60,000 centistokes (Viscasil, GEC)
(4) Polymer JR 400
(5) Carbopol 941 (BF Goodrich)

EXAMPLES 27 TO 28

The following formulations represent lotions which can be used topically in the treatment of bald or balding male or female heads.

|  | % w/w | |
|---|---|---|
|  | 27 | 28 |
| Hydroxyethyl cellulose | 0.4 | — |
| Absolute ethanol | 25 | 25 |
| Propane-1,2-diol | — | — |
| Butane-1,3-diol | 38.4 | 38.8 |
| Paramethyl benzoate | 0.2 | 0.2 |
| Inhibitor No. 27 | 5 | — |
| Inhibitor No. 28 | — | 1 |
| Perfume | 1 | 1 |
| Water to | 100 | 100 |

EXAMPLE 29

The following example illustrates a lotion according to the invention which can be applied topically to the scalp to prevent hair loss and stimulate hair regrowth.

| | % w/w |
|---|---|
| Inhibitor No. 29 | 7 |
| Minoxidil | 0.2 |
| ethanol | 16 |
| citric acid | 1.05 |
| water to | 100 |
| pH adjusted to 4.2 with sodium hydroxide | |

EXAMPLE 30 AND 31

These examples illustrate hair tonics which are suitable for application to the hair and scalp.
The hair tonics had the following formulation:

| | % w/w | |
|---|---|---|
| | 30 | 31 |
| Inhibitor No. 30 | 2 | — |
| Inhibitor No. 31 | — | 3 |
| Minoxidil | — | 0.5 |
| ethanol | 50 | 50 |
| water | 48 | 47 |
| perfume | q.s. | q.s. |

We claim:
1. A composition suitable for topical application to mammalian skin or hair for inducing, maintaining or increasing hair growth which comprises:
   (i) an effective amount of a glycosaminoglycanase inhibitor selected from:
   (a) aldonomonolactone or alduronomonolactone derivatives having the structure:

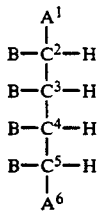

where
$A^1$ is

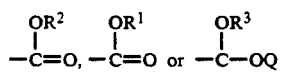

$A^6$ is

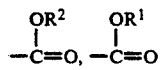

or $-CH_2 OR^3$
B is $-OR^3$, $-NHR^3$, $-NHR^4$, or a lactone linkage to position 1 or 6, and/or an ether linkage to Q;
said substituents B being the same or different, and being in either configuration, with respect to the backbone of the above structure, on positions $C^2$ to $C^5$ not involved in a lactone ring;
and where
$R^1$ is $-H$, $C_1$ to $C_{20}$ alkyl, a metal cation, $NH_4+$ or an alkanolamine cation;

$R^2$ is the remainder of the molecule joined through another C atom at positions 2 to 5 to form a lactone,
$R^3$ is $-H$, $-CH_3$, benzyl or $C_2$ to $C_6$ acyl;
$R^4$ is $-H$, $-CH_3$, benzyl or $C_3$ to $C_6$ acyl;
Q is the remainder of the molecule joined through an ether ring selected from pyranose with linkage to $C^4$ and furanose with linkage to $C^5$;

provided that either $A^1$ or $A^6$ is $-C=O$;
provided also that, when $A^6$ is $CH_2OH$, then one or more of the B substituents is $OR^3$ in which $R^3$ is $-CH_3$ or $C_2$ to $C_4$ acyl, or is $NHR^3$;
provided also that when $A^1$ is

and all B substituents are $-OH$, then
$A^6$ is $$\begin{array}{c} OR^1 \\ | \\ -C=O \end{array}$$

or $-CH_2OR^3$, and $R^1$ is $C_1$ or $C_9$ to $C_{20}$ alkyl;
(b) acylated monosaccharides having the structure:

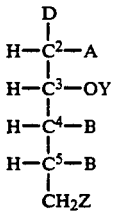

where A or $-OY$ or $-NHR^5$
B is $-OY$, or an ether linkage to D,
D is $-CHOY$, where X is an ether

X ring selected from pyranose with linkage to $C^4$ and furanose with linkage to $C^5$;
Y is $-H$, $-SO_3M$, $C_2$ to $C_4$ acyl or $C_1$ to $C_{18}$ alkyl;
said substituents A, B & OY being the same or different, and being in either configuration, with respect to the backbone of the structure;
and where
Z is $-H$ or $-OY$
$R^5$ is $-H$, $-SO_3M$ or $C_3$ or $C_4$ acyl,
M is $-H$, a metal cation, $NH_4+$ or an alkanolamine cation,
provided that, when $R^5$ is $-H$, or when A is OY, then 1 or more of Y is chosen from $-SO_3M$ or $C_2$ to $C_4$ acyl; and mixtures thereof; and
(ii) a cosmetically acceptable vehicle for the inhibitor; the effective amount of the inhibitor present in the composition being sufficient to increase hair growth in the rat, when said composition is applied topically thereto over a period of no more than 3 months, by at least 10% more than that obtainable using a control composition from which the said inhibitor has been omitted, in accordance with the Rat Hair Growth Test.

2. The composition of claim 1, wherein the glycosaminoglycanase inhibitor is an aldonomonolactone selected from the group consisting of:
  6-acetyl-galactono-1,4-lactone
  6-propionyl-galactono-1,4-lactone
  6-butyryl-galactono-1,4-lactone
  2-propionamido-2-deoxygluconolactone
  2-butyramido-2-deoxygluconolactone
  2-propionamido-2-deoxygalactonolactone
  2-butyramido-2-deoxygalactonolactone
  6-propionyl-2-acetamido-2-deoxygluconolactone
  diacetyl-6-propionyl-2-acetamido-2-deoxygluconolactone
  6-butyryl-2-acetamido-2-deoxygalactonolactone
  diacetyl-6-butyryl-2-acetamido-2-deoxygalactonolactone
  2,3,5,6-tetraacetyl-galactono-1,4-lactone
  2,3,5-triacetyl-6-propionylgalactono-1,4-lactone
  triacetyl-2-propionamido-2-deoxygalactonolactone
  triacetyl-2-butyramido-2-deoxygluconolactone
  6-methyl-glucaro-1,4-lactone
  2,3,5,6-tetramethyl-glucaro-1,4-lactone
  6-methyl-2,3,5-triacetylglucaro-1,4-lactone
  6-methyl-3-methyl-glucaro-1,4-lactone, and
  6-methyl-3-acetyl-glucaro-1,4-lactone.

3. The composition of claim 1, wherein the glycosaminoglycanase inhibitor is the alduronomonolactone:
  1,2,5-triacetyl-glucurono-6,3-lactone.

4. The composition of claim 1, wherein the glycosaminoglycanase inhibitor is an acylated monosaccharide selected from the group consisting of:
  2-propionamido-2-deoxyglucose
  1,3,4,6-tetraacetyl-2-propionamido-2-deoxyglucose
  2-butyramido-2-deoxygalactose
  1,3,4,6-tetraacetyl-2-butyramido-2-deoxygalactose
  2-sulphamido-2-deoxygalactose
  2-sulphamido-2-deoxyglucose
  2-butyramido-2-deoxymannose
  1,3,4,6-tetraacetyl-2-butyramido-2-deoxymannose
  2-butyramido-2-deoxyglucose, and
  1,3,4,6-tetraacetyl-2-butyramido-2-deoxyglucose.

5. The composition of claim 1, wherein the effective amount of glycosaminoglycanase inhibitor present in the composition is sufficient to increase hair growth in the rat by at least 20%.

6. The composition of claim 1, wherein the effective amount of the inhibitor present in the composition is from 0.0001 to 99% by weight.

7. The composition of claim 1, wherein the cosmetically acceptable vehicle forms from 1 to 99.99% by weight of the composition.

8. The composition of claim 1, which further comprises from 0.01 to 10% by weight of a perfume.

9. A method for converting vellus hair to growth as terminal hair which comprises the step of applying to the scalp in the region of vellus hair an effective amount of the composition according to claim 1.

10. A method for increasing the rate of terminal hair growth, which comprises the step of applying to the scalp in the region of terminal hair an effective amount of the composition according to claim 1.

* * * * *